(12) United States Patent
Hainsworth et al.

(10) Patent No.: US 12,214,129 B2
(45) Date of Patent: Feb. 4, 2025

(54) LARYNGEAL MASK AIRWAY DEVICE AND METHOD FOR ADMINISTERING A MEDICAMENT THROUGH A LARYNGEAL MASK AIRWAY DEVICE

(71) Applicant: Chiesi Farmaceutici S.p.A., Parma (IT)

(72) Inventors: John Kenneth Hainsworth, Cambridge (GB); George Robert Butcher, Cambridge (GB); Peter Ryan Smith, Cambridge (GB); Thomas Henry Shaw, Cambridge (GB); Anthony Robinson, Cambridge (GB)

(73) Assignee: Chiesi Farmaceutici S.p.A., Parma (IT)

( * ) Notice: Subject to any disclaimer, the term of this patent is extended or adjusted under 35 U.S.C. 154(b) by 825 days.

(21) Appl. No.: 17/298,382

(22) PCT Filed: Nov. 29, 2019

(86) PCT No.: PCT/EP2019/083026
§ 371 (c)(1),
(2) Date: May 28, 2021

(87) PCT Pub. No.: WO2020/114895
PCT Pub. Date: Jun. 11, 2020

(65) Prior Publication Data
US 2022/0111168 A1    Apr. 14, 2022

(30) Foreign Application Priority Data
Dec. 6, 2018  (EP) .................................. 18210791

(51) Int. Cl.
*A61M 16/04*    (2006.01)
*A61B 1/00*     (2006.01)
*A61B 1/06*     (2006.01)
*A61B 1/267*    (2006.01)
*A61M 16/08*    (2006.01)

(52) U.S. Cl.
CPC ..... *A61M 16/0409* (2014.02); *A61B 1/00098* (2013.01); *A61B 1/00135* (2013.01);
(Continued)

(58) Field of Classification Search
CPC ........... A61M 16/04–0497; A61M 25/00–104; A61M 2025/0001–1097; A61B 1/00–32
(Continued)

(56) References Cited

U.S. PATENT DOCUMENTS

| | | | |
|---|---|---|---|
| 5,743,258 A * | 4/1998 | Sato | A61M 16/0484 128/207.14 |
| D752,215 S | 3/2016 | Blennow | |

(Continued)

FOREIGN PATENT DOCUMENTS

| | | |
|---|---|---|
| CN | 103118731 A | 5/2013 |
| CN | 204582218 U | 8/2015 |

(Continued)

OTHER PUBLICATIONS

Translation of WO-2019146068-A1. Accessed from PE2E on Sep. 11, 2024. (Year: 2019).*

(Continued)

*Primary Examiner* — Valerie L Woodward
*Assistant Examiner* — Paige Kathleen Bugg
(74) *Attorney, Agent, or Firm* — Sterne, Kessler, Goldstein & Fox P.L.L.C.

(57) ABSTRACT

A laryngeal mask airway device includes an airway tube and a laryngeal mask placed at a distal end of the airway tube. The distal end of the airway tube opens inside the laryngeal mask. The device includes a connector placed at a proximal end of the airway tube. The connector is in fluid communication with the laryngeal mask through the airway tube and is configured to be connected to a ventilation equipment. The device includes a movable element placed in the laryn- (Continued)

geal mask and configured to steer a tip of a catheter passing through the airway tube. The device further includes a control element mounted on the proximal end of the airway tube and a motion transmission device operatively connected to the movable element and to the control element to move the movable element and to steer the tip of the catheter by acting on the control element.

26 Claims, 8 Drawing Sheets

(52) U.S. Cl.
CPC ............... *A61B 1/06* (2013.01); *A61B 1/267* (2013.01); *A61M 16/0463* (2013.01); *A61M 16/0488* (2013.01); *A61M 16/0816* (2013.01); *A61M 2205/502* (2013.01); *A61M 2205/587* (2013.01)

(58) Field of Classification Search
USPC .................................................. 128/207.15
See application file for complete search history.

(56) References Cited

U.S. PATENT DOCUMENTS

| | | | |
|---|---|---|---|
| D775,330 S | 12/2016 | Blennow | |
| 2005/0267327 A1* | 12/2005 | Iizuka | A61B 1/00133 600/106 |
| 2007/0197871 A1* | 8/2007 | Geitz | A61B 1/018 600/117 |
| 2012/0255551 A1* | 10/2012 | Boussignac | A61M 16/0484 128/204.18 |
| 2015/0351610 A1* | 12/2015 | Fan | A61B 1/0052 600/148 |
| 2018/0169365 A1* | 6/2018 | Sawyer | A61M 16/0434 |
| 2019/0054266 A1* | 2/2019 | Sun | A61M 16/0447 |
| 2019/0351167 A1* | 11/2019 | Musuku | A61H 7/00 |

FOREIGN PATENT DOCUMENTS

| | | |
|---|---|---|
| CN | 107823767 A | 3/2018 |
| WO | 2004/016308 A2 | 2/2004 |
| WO | 2008/071977 A1 | 6/2008 |
| WO | 2008/148469 A1 | 12/2008 |
| WO | 2011/126812 A1 | 10/2011 |
| WO | 2012/032290 A1 | 3/2012 |
| WO | 2014/089028 A1 | 6/2014 |
| WO | WO-2019146068 A1 * | 8/2019 |

OTHER PUBLICATIONS

International Search Report issued in International Application No. PCT/EP2019/083026, mailed Feb. 3, 2020, 4 pages.

* cited by examiner

FIG.7
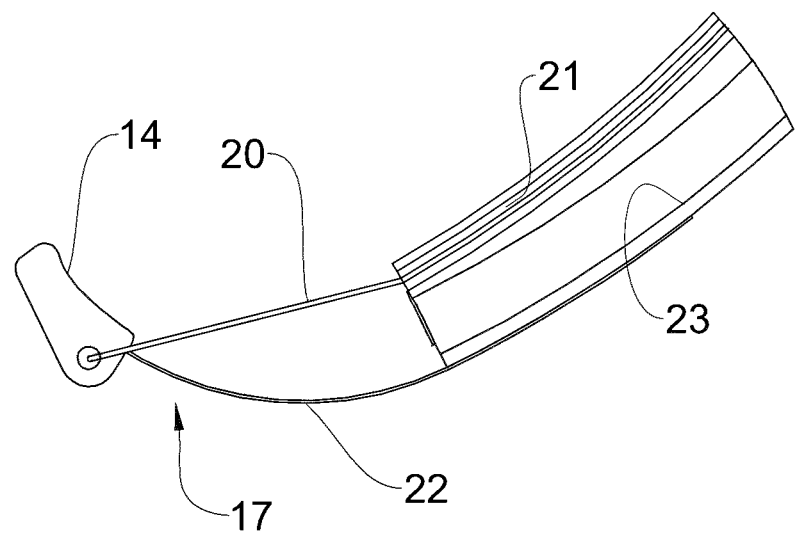
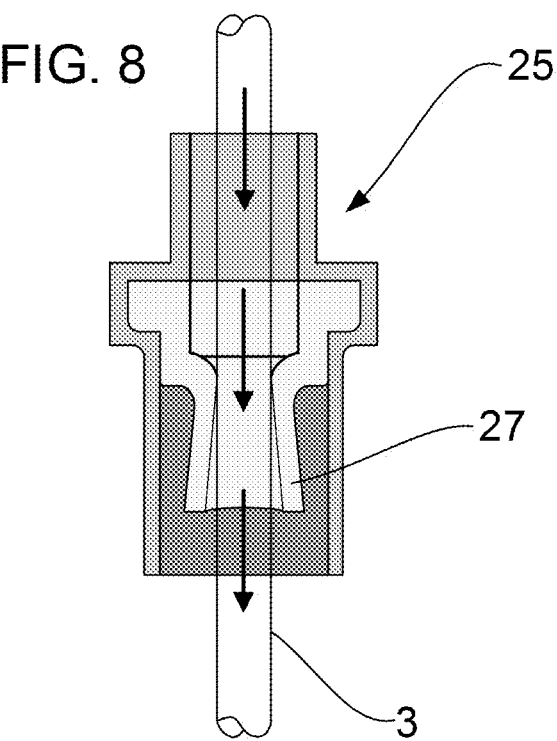
FIG. 8
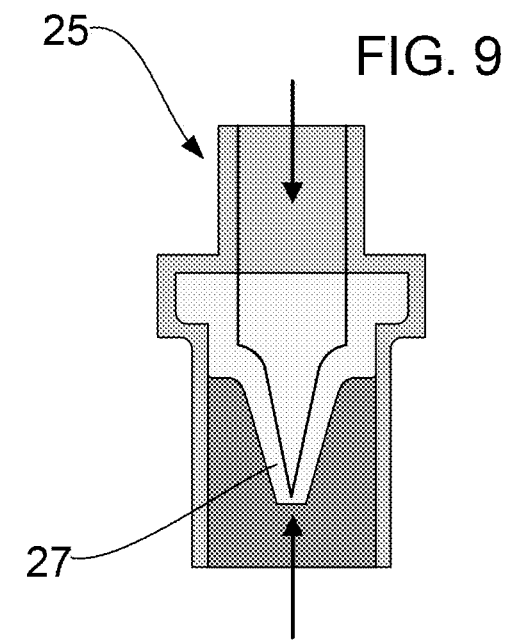
FIG. 9

LARYNGEAL MASK AIRWAY DEVICE AND METHOD FOR ADMINISTERING A MEDICAMENT THROUGH A LARYNGEAL MASK AIRWAY DEVICE

BACKGROUND OF THE INVENTION

The present invention relates to a laryngeal mask airway device and to a method for administering a medicament through a laryngeal mask airway device. In particular, the present invention relates to administration of medicaments through a catheter inserted and guided through a laryngeal mask airway device. More in particular the invention relates to surfactant administration to premature newborns through a laryngeal mask airway device.

In the case of respiratory diseases, it is sometimes necessary to deliver medicaments directly into the lungs. Respiratory Distress Syndrome (RDS) is an example of such a disease, in which the patient has a deficiency in pulmonary surfactant. Pulmonary surfactant is a substance naturally found in the lungs, which reduces alveolar collapse by decreasing surface tension in the alveoli. This condition affects more particularly newborns and is a major cause of mortality in premature neonates. It has been observed that the more premature the neonate, the less pulmonary surfactant production because of lung immaturity and the higher the probability for RDS.

Standard surfactant replacement therapy requires the distribution of a volume of liquid formulation of an exogenous pulmonary surfactant to the lungs of a premature neonate, kept under mechanical ventilation by means of an endotracheal tube.

Current methods to achieve this require a high degree of clinical skill, and present considerable risks of local and systemic trauma to the patient.

A laryngoscope is used to intubate the patient with said endotracheal tube, and then a bolus of surfactant is then injected through the tube. It is well known that several risks might be associated to this method. Indeed, use of laryngoscope causes pain and stress to patient with associated systemic response. Contact of the endotracheal tube with tracheal mucosa is also highly invasive with possible associated systemic response and local trauma risk to trachea and vocal cords.

Undetected esophageal intubation or dislocated endotracheal tube may occur due to limited view offered by laryngoscope and this may lead to injection of surfactant into the esophagus, resulting in loss of treatment efficacy and potential esophageal insufflation. Trauma to lungs due to positive pressure ventilation may also occur.

Therefore, the new guidelines for the treatment of the preterm neonates suggest avoiding the use of invasive ventilation whenever it is possible and preferring non-invasive approaches, which means that neonates are no longer intubated if it is not strictly necessary and consequently they would be intubated just for the administration of the surfactant. All these modalities rely on the premise that preterm neonates are spontaneously breathers.

In these cases, as a possible respiratory support, the use of non-invasive ventilation modalities such as early Continuous Positive Airway Pressure (CPAP) or High Flow Nasal Cannula (HFNC), that delivers air into the lungs through specifically designed nasal devices such as masks, prongs or tubes, were introduced in neonatal intensive care units (NICUs).

Following this orientation, in the last fifteen years great attention was paid to finding alternative, less invasive methods for pulmonary surfactant administration, possibly in combination with non-invasive ventilation support.

For example, the use of a gastric tube placed in the trachea supported with nCPAP has been proposed in WO 2008/148469. Similar devices such as vascular catheters or nasogastric tubes were also disclosed in the art (Dargaville PA et al Arch Dis Fetal Neonatal Ed 2013, 98(2), 122-126.

However, even with these methods, a laryngoscope shall be used to provide visual access to the laryngeal inlet and forceps are then used to feed the catheter into the laryngeal inlet.

Applicant perceived that several risks are associated also to these known methods.

Indeed, use of forceps in oropharynx requires high skill level and presents risk of local trauma. Lack of ventilation support (CPAP) during procedure may increase risk of hypoxia. Since no immediate means to provide mechanical ventilation in the event that rescue is required, emergency intubation with associated risks may be necessary.

Document WO 2008/071977 is also known, which discloses a laryngeal mask airway device comprising an airway tube extending from a proximal end to a distal end and opening, at the distal end, into the interior of a hollow mask portion shaped to fit into the actual and potential space behind the larynx and to seal around the circumference of the laryngeal inlet without penetrating into the interior of the larynx. The device comprises a conduit adapted to direct a liquid substance through the glottic opening.

Document WO 2012/032290 discloses a laryngeal mask airway device, wherein the mask portion of the device includes guiding means adapted such that, when the laryngeal mask airway device is in use with a drug delivery catheter, the guiding means guides the drug delivery catheter towards the larynx.

Applicant perceived that also the solutions of these last two mentioned patents can be improved, in particular with reference to accuracy of guiding the catheter and ease of use of the device.

BRIEF SUMMARY OF THE INVENTION

It is an object of the present invention to improve precision and ease of use of the known laryngeal mask airway devices used with medicament delivery catheters. In particular, it is an object of the present invention to increase catheter position control, in order to avoid or significantly reduce risk of tissue damage and to grant a lower level of invasiveness.

It is also object of the present invention to make the catheter position control easier for the clinician.

Another object of the present invention is to improve overall breathing of patients that require treatment with laryngeal mask airway devices.

At least one of the above objects is substantially achieved by a laryngeal mask airway device and by a method for administering a medicament through said laryngeal mask airway device according to one or more of the appended claims and/or of the following aspects.

Aspects of the invention are disclosed in the following.

In accordance with a $1^{st}$ independent aspect, a laryngeal mask airway device comprises:
- an airway tube having a proximal end and a distal end;
- a laryngeal mask placed at the distal end of the airway tube, wherein the distal end of the airway tube opens inside the laryngeal mask, wherein the laryngeal mask is shaped like a bowl and is configured to seal around a laryngeal inlet of a patient;

a connector placed at the proximal end or close to the proximal end of the airway tube, wherein the connector is in fluid communication with the laryngeal mask through the airway tube and is configured to be connected to a ventilation equipment;

a movable element placed in the laryngeal mask and configured to steer a tip of a catheter passing through the airway tube when said catheter protrudes in the laryngeal mask;

a control element;

a motion transmission device operatively connected to the movable element and to the control element to move the movable element and to steer the tip of the catheter by acting on the control element;

wherein the control element is mounted on the proximal end of the airway tube. In accordance with a $2^{nd}$ independent aspect, a laryngeal mask airway device comprises:

an airway tube having a proximal end and a distal end;

a laryngeal mask placed at the distal end of the airway tube, wherein the distal end of the airway tube opens inside the laryngeal mask, wherein the laryngeal mask is shaped like a bowl and is configured to seal around a laryngeal inlet of a patient;

a connector placed at the proximal end or close to the proximal end of the airway tube, wherein the connector is in fluid communication with the laryngeal mask through the airway tube and is configured to be connected to a ventilation equipment;

wherein such laryngeal mask airway device further comprises an exhalation channel, such exhalation channel having one of its ends in fluid communication with the distal end of the airway tube, and the other end being an outlet to air.

In accordance with a $3^{rd}$ independent aspect, a method for administering a medicament through a laryngeal mask airway device is provided, wherein the laryngeal mask airway device is according to the first or second aspects or to one or more of the following aspects.

In a $4^{th}$ independent aspect, a method for administering a medicament through a laryngeal mask airway device comprises:

inserting an airway tube of a laryngeal mask airway device into an oropharynx of a patient and sealing a laryngeal mask placed at a distal end of the airway tube around a laryngeal inlet of the patient;

optionally, connecting a connector placed at a proximal end or close to the proximal end of the airway tube to a ventilation equipment;

passing a catheter through the airway tube until a tip of the catheter protrudes into the laryngeal mask;

handling a control element mounted on the proximal end of the airway tube to move, through a motion transmission device, a movable element placed in the laryngeal mask and in contact with a tip of the catheter in order to steer said tip and to align it with the laryngeal inlet;

advancing the tip to a position below the vocal cords;

injecting a medicament through the catheter.

In accordance with a $5^{th}$ independent aspect, an assembly or kit comprises a laryngeal mask airway device according to the first aspect or to one or more of the following aspects and at least a catheter and, preferably, a package for the device and the catheter.

In a $6^{th}$ aspect, a method for preventing and/or treating a respiratory distress syndrome in a spontaneously breathing patient is provided, said method comprising applying the device herein disclosed in combination with a catheter for the delivery of a medicament.

The airway tube terminating in a bowl provides a passage from outside the patient's mouth to the glottis. The connector allows the airway tube to be connected to ventilation equipment. The movable element, control element and motion transmission device allow to accurately adjust the orientation of the distal end of the catheter to bring it in line with the laryngeal inlet, such that it can be passed accurately through the vocal cords. The control element placed on the proximal end allows the user/clinician to orient the tip of the catheter easily and accurately. The exhalation channel allows exhalation of exhaled air by the patient that may otherwise be trapped in the dead volume of the laryngeal mask airway device and re-breathed by the patient.

In an aspect, the motion transmission device is a mechanical device.

In an aspect, the motion transmission device is inserted or incorporated within the airway tube.

In an aspect, the control element comprises an external portion protruding from the proximal end and configured to be handled by a user.

In an aspect, the control element comprises an internal portion placed inside the proximal end and connected to the motion transmission device.

In an aspect, the control element comprises a handle, a lever, a button or a joystick.

In an aspect, the external portion is a handle, a lever, a button or a joystick.

In an aspect, the movable element is movable between a first position, in which it lies against an inner surface of the laryngeal mask, and a second position, in which it protrudes into the laryngeal mask to steer the tip of the catheter.

In an aspect, the control element is movable at least between a first position and a second position corresponding to the first position and the second position of the movable element.

In an aspect, the control element comprises a shaft axially movable between the first position and the second position.

In an aspect, in the first position the shaft is mainly extracted from the proximal end and in the second position the shaft is mainly retracted in the proximal end.

In an aspect, a box-like casing defines the proximal end and supports the connector and the control element.

In an aspect, the box-like casing delimits internally a chamber in fluid communication with the connector.

In an aspect, the box-like casing delimits internally a housing for the internal portion of the control element.

In an aspect, the airway tube delimits internally a ventilation conduit in fluid communication with the connector and optionally with the chamber.

In an aspect, the ventilation conduit opens in the laryngeal mask.

In an aspect, the airway tube delimits or comprises at least one guide element for the catheter. This way, the catheter may be guided towards the laryngeal inlet.

In an aspect, said at least one guide element is a guide channel extending along the airway tube.

In an aspect, the guide channel is other than the ventilation conduit.

In an aspect, the guide channel is inside the ventilation conduit.

In an aspect, the guide channel is substantially parallel to the ventilation conduit.

In an aspect, said at least one guide element comprises a plurality of guide elements disposed along the airway tube.

In an aspect, the plurality of guide elements is placed inside the ventilation conduit, optionally on an inner wall of the ventilation conduit.

In an aspect, a catheter port for inserting the catheter is delimited on the proximal end.

In an aspect, the catheter port communicates with the guide channel.

In an aspect, the catheter port comprises a self-sealing opening to close said catheter port. The self-sealing opening prevents air leakage when the catheter is not inserted. The self-sealing opening allows to insert the catheter whilst preventing air leakage. This enables the continuous provision of effective Continuous Positive Airway Pressure (CPAP) respiratory support throughout the medicament administration procedure. It also enables the provision of positive pressure ventilation (PPV) at any point during the procedure if a situation requiring rescue ventilation develops.

In an aspect, the self-sealing opening comprises an elastomeric component which creates a seal, whilst allowing the catheter to slide with low resistance as the user inserts/retracts it. The elastomeric component completely closes and resists leakage when the catheter is removed. The elastomeric component may be a 'normally closed' elastomeric valve, for example a silicone 'duckbill' valve, which automatically seals even when the catheter has been removed.

In an aspect, the catheter port comprises a sealing cap. The port may be a simpler seal such as an 'O-ring', which provides the main sliding seal when the catheter is in the laryngeal mask airway device, but with a sealing cap that the user manually closes, to seal the catheter port when the catheter is not in place.

In an aspect, the catheter port is fashioned in the box-like casing.

In an aspect, the catheter port is placed on the top face of the box-like casing opposite the airway tube.

In an aspect, the catheter port is placed on a side of the box-like casing.

In an aspect, the airway tube comprises or delimits at least one seat for at least part of the motion transmission device.

In an aspect, the airway tube is flexible.

In an aspect, the airway tube is made of PVC, silicone, elastomer or combination of multiple materials.

In an aspect, the catheter is flexible, preferably elastically flexible.

In an aspect, a catheter for minimally invasive endotracheal administration of a pulmonary surfactant is used, for example according to procedure disclosed in WO 2008/148469 or in Dargaville PA et al Arch Dis Fetal Neonatal Ed 2013, 98(2), 122-126.

In an aspect, the catheter has a diameter equal to or lower than 5 French (Fr) corresponding to about 1.66 mm (1 French corresponds to ⅓ mm). Preferably, the diameter is between 2.0 and 5.0 Fr. Preferred diameters are 3.5, 4.0 and 5.0 Fr.

Preferably, the catheter is according to document USD775330 or USD752215.

In an aspect, any gastric or nasogastric tube, arterial or suction catheter of common use in hospitals may be utilized. Preferably, the catheter is made of polyurethane or silicone. Preferably, the catheter has a length from 10 cm to 35 cm, preferably of 15 cm or 30 cm.

In an aspect, the airway tube is anatomically shaped, in order to reduce forces on the anatomy.

In an aspect, said at least one seat is other than the ventilation conduit.

In an aspect, said at least one seat comprises a passage or a plurality of passage sections for at least part of the motion transmission device.

In an aspect, the motion transmission device comprises a cord or a rod.

In an aspect, the motion transmission device comprises a spring.

In an aspect, the spring is a leaf spring.

In an aspect, the cord or rod has a proximal extremity linked to the control element, optionally to the internal portion of the control element, and a distal extremity linked to the movable element.

In an aspect, the movable element is pulled or pushed by the control element through the cord or rod, preferably in opposition to an elastic force exerted by the spring. Preferably, the spring returns to its start position/configuration when the control is released.

In an aspect, the movable element is mounted to an end of the spring and an extremity of the cord is linked to the movable element or to said end of the spring so that the spring is elastically deflected by pulling the cord.

In an aspect, the spring and the movable element are made in one piece as a single item.

In an aspect, the spring comprises a part joined to the airway tube or motionless with respect to the airway tube and the end of the spring is cantilevered.

In an aspect, the spring is located on a side of the airway tube opposite the cord, wherein the catheter passes between the cord and the spring.

In an aspect, the cord is pulled when the shaft moves towards the second position.

In an aspect, the spring is absent and the movable element remains in the second position and/or must be moved, through the control element and the motion transmission device, from the first position to the second position and from the second position to the first position.

In an aspect, the motion transmission device and the movable element are jointly attached, whereby they are made in one piece as a single item.

In an aspect, the motion transmission device comprises a stem and the movable element comprises a hooked tip. The stem is jointly attached to its distal end to the hooked tip, whereby at least the stem and the hooked tip are made in one piece as a single item.

In an aspect, the stem is moveably arranged in the laryngeal mask airway device such that it can move at least along an axis when the control element is operated, optionally such axis is substantially parallel to the longitudinal axis of the airway tube.

In an aspect, the hooked tip is moveably arranged in the laryngeal mask airway device such that it can rotate about an axis when at least the stem moves. Optionally, the axis about which the hooked tip rotates is substantially perpendicular to the longitudinal axis of the airway tube. Accordingly, operating the control element provides movement of the motion transmission device comprising the stem and the rotation of the movable element comprising the hooked tip. The rotation of the hooked tip allows deflecting the catheter whereby it can be orientated with respect to the laryngeal mask airway device and therefore with respect to the patient anatomy.

In an aspect, the motion transmission device comprises a linking interface jointly attached to the proximal end of the stem, whereby at least the stem, the hooked tip and the linking interface are made in one piece as a single item.

In an aspect, the linking interface is linked to the control element, optionally to the internal portion (e.g. the shaft) of the control element, whereby acting the control element causes a movement in the linking interface. As the linking interface, the stem and the hooked tip are made in one piece as a single item, the movement of the linking interface moves the stem and rotates the hooked tip.

In an aspect, the linking interface has a wedge contacting a respective wedge of the shaft of the control element. Such wedges are arranged to be slidingly moveable relative to each other, whereby axial movement of the shaft from the first position to the second position causes a respective movement of the linking interface, optionally a movement substantially perpendicular relative to the axial movement of the shaft.

In an aspect, at least part of the stem is able to axially transmit force (e.g. tension) at least from its proximal end to its distal end. Accordingly, at least part of the stem is made of a flexible material, such as plastic, so that force/tension can be axially transmitted from the linking interface to the hooked tip. Optionally, the linking interface, the stem and the hooked tip are made of a flexible material such, as plastic.

In an aspect, the motion transmission device further comprises a spring mounted at or near the linking interface.

In an aspect, the spring abuts at one of its ends against a stationary element, e.g. against a surface of the interior wall of the box-like casing, and at the other end against a pushing surface of the linking interface, whereby the spring is tensioned when the linking interface is moved by acting the control element, and the spring is discharged when the control element is released. Discharge of the spring causes the return of the linking interface, of the stem, of the hooked tip and of the control element to their start position/configuration.

In an aspect, the movable element also comprises an anchor point configured to contact a respective anchor point at the distal end of the airway tube, whereby the anchor points of the movable element and the respective anchor point of the airway tube form a hinge about which the hooked tip can rotate.

In an aspect, the movable element further comprises a flexible section jointly attached to the distal end of the stem. In an aspect, the distal end of stem converges into the flexible section, whereby the flexible section of the hooked tip is thinner with respect to the stem. The flexible section provides a high level of bending of the hooked tip and a following high degree of deflection of the catheter.

In an aspect, at least part of the motion transmission device and/or at least part of the movable element abut against a stationary surface, for example against an inner wall of the seat delimited in the airway tube, whereby movement of the stem and the linking interface is resisted by the stationary surface and/or by the hinge formed by the two anchor points. Such resistances cause bending of at least the flexible section when the stem and the linking interface move, whereby the hooked tip rotates and the catheter can be deflected.

In an aspect, a visualization system is placed at the distal end and inside the laryngeal mask.

In an aspect, a camera is placed at the distal end and inside the laryngeal mask.

In an aspect, an illumination source is placed at the distal end and inside the laryngeal mask.

In an aspect, the camera, and optionally the illumination source, are part of an endoscope.

In an aspect, the endoscope passes through a dedicated channel fashioned in the airway tube or placed inside the airway tube.

In an aspect, the endoscope is removably inserted into the dedicated channel.

In an aspect, the illumination source comprises a stand-alone light fiber or light guide.

In an aspect, an end of said dedicated channel facing outwards the ventilation channel is closed by a transparent cap to protect the endoscope and/or a stand-alone light fiber or light guide.

In an aspect, the camera, and optionally the illumination source, face outwards the ventilation channel to frame the movable element and the catheter tip.

The camera and the illumination source located in the distal end of the airway device may be positioned to give a view of the vocal cords and catheter as it advances into the laryngeal inlet. The visualization system provides the user with the required visual feedback to safely and effectively perform the procedure, without the need to force the patient's airway anatomy into alignment. The use of the visualization system also enables the effective use of the active catheter orientation, as the direct visual feedback allows the user to precisely judge the correct adjustment of catheter position required to align the catheter with the patient's laryngeal inlet.

In an aspect, the camera is connected to an electronic display screen.

The electronic display screen presents a live view from the camera to the clinician.

In an aspect, the laryngeal mask comprises a cuff.

In an aspect, the cuff is inflatable.

In an aspect, the cuff is non-inflatable, and optionally can be made by a material selected from poly-vinyl chloride (PVC), thermoplastic elastomers such as the styrenic block copolymers (e.g. styrene butadiene styrene (SBS), styrene ethylene butylene styrene (SEBS)), and thermoplastic olefin blends (TPO), thermoplastic poly-urethanes (TPU), thermoplastic vulcanisates (TPV), copolyester (COPE), polyether block amides (PEBAX), melt processable rubbers, flexible co-polymers such as EVA, and foamed versions thereof, where appropriate. Suitable cuffs according to the present aspect can be the ones made from the materials and manufactured according to WO 2004/016308.

In an aspect, an inflation line is connected to the cuff.

In an aspect, the inflation line comprises an inflation tube optionally joined to the airway tube or fashioned in the airway tube.

In an aspect, the laryngeal mask airway device assembly is, in part or in-toto, reusable or disposable.

In an aspect, the airway tube is removably connected to the box-like casing.

In an aspect, the airway tube and the laryngeal mask and optionally the visualization system are disposable.

In an aspect, the guide element for the catheter, the movable element and the motion transmission device and optionally the visualization system are removable from the airway tube.

In an aspect, the control element, the guide element for the catheter, the movable element and the motion transmission device, and optionally the visualization system, are reusable.

In an aspect, the guide channel for the catheter is delimited by a tubing joined to the box-like casing.

In an aspect, the passage for the cord is delimited by a tubing joined to the box-like casing.

In an aspect, the spring is integral with a tubing delimiting the guide channel.

In an aspect, the visualization system is integral with the airway tube or with a tubing delimiting the guide channel.

In an aspect, the connector of the laryngeal mask airway device is configured to be connected at a first end to the ventilation equipment and at a second end to the airway tube, optionally to the ventilation conduit of the airway tube. The first end and the second end are in fluid communication with each other. The second end has a smaller section area than a section area of the first end. The connector also comprises external walls configured to engage with the ventilation equipment, and internal walls, delimiting the internal space of the controller. The controller is characterized in that the internal walls converge from the first end to the second end. Accordingly, the internal walls can have for example truncated cone geometry, truncated pyramid geometry, or any other geometry such that the internal walls converge from the first end to the second end without abrupt narrowing, e.g. without steps.

Applicant verified that this geometry of the internal walls of the connector is particularly advantageous when ventilation through laryngeal mask airway device is required, especially for patients with small tidal volumes such as pre-term neonates. Indeed, this geometry allows reducing the flow resistance with respect to conventional geometry of the internal walls of known connectors, as the latter narrow down abruptly from the first end to the second end, providing a sudden contraction to the flow of air. On the contrary, the connector as described above provides a streamlined transition from the first end to the second, smaller end, thus reducing the air flow resistance and reducing the work of breathing of patients.

The external walls of the connector are advantageously configured to be coupled with standard female connections of conventional ventilation equipment, in particular at or near its first end.

In an aspect, the external walls of the connector comprise one or more fins, such one or more fins protruding outwards from the internal walls (outwards with respect to the internal space of the connector). This is useful to to enhance moldability of the connector.

In an aspect, such one or more fins are at least two, and protrude from the internal walls for a length such that they are flush with one another.

In an aspect, the thickness of the internal walls and of each of the one or more fins is (substantially) the same.

Fins allow maintaining a suitable outer diameter such that it is possible to couple standard female connections of conventional ventilation equipment to the connector, and at the same time they allow improving the overall industrial manufacturability of the connector. Indeed, several conventional manufacture processes for articles such as the connector (e.g. injection molding) require that components have similar thicknesses. Accordingly, each fin can advantageously have similar thickness with respect to each other and to the internal walls, improving the moldability of the connector.

In an aspect, the medicament is a surfactant administered to premature newborns.

In an aspect, following medicament administration, the catheter is removed and the catheter port is closed. The laryngeal mask airway device may be used to provide positive pressure ventilation to recover bradycardia or hypoxia.

The inflatable cuff at the end of the bowl is shaped to form a seal around the glottis. The inflation line allows the cuff to be inflated and deflated using for example a syringe.

In an aspect, the method of the invention comprises applying to the patient a non-invasive ventilation procedure such as nasal Continuous Positive Airway Pressure (nCPAP). Preferably, a nasal mask or nasal prongs are utilized.

In an aspect, nasal CPAP is applied at a pressure comprised between 1 and 12 cm $H_2O$, preferably 2 and 8 cm $H_2O$.

Other non-invasive ventilation procedures, such as nasal intermittent positive-pressure ventilation (NIPPV) and bi-level positive airway pressure (BiPAP) or high flow nasal cannula (HFNC), may alternatively be applied to the patients.

In an aspect, the laryngeal mask airway device may be manufactured in different sizes that are dimensioned to fit a range of neonatal patients, which may include full-term newborns to very premature newborns, preferably premature newborns, more preferably very-low-weight-birth premature neonates.

Applicant verified that the laryngeal mask airway device according to the invention allows a clinician to manipulate the orientation of the tip of the catheter in an accurate and easy way.

Indeed, the clinician may hold the proximal end of the airway tube and handle the control element, e.g. with a finger, to adjust the position of the movable element.

When the catheter is inserted into the laryngeal mask airway device, the catheter is guided by the guide element/s which causes the catheter tip to come into proximity with the movable element. When the movable element is moved via the control element and the motion transmission device, the movable element (catheter deflector) pushes on the tip of the catheter, adjusting its orientation with respect to the laryngeal mask airway device and therefore with respect to patient anatomy.

Advantageously, the device of the invention is used in combination with a catheter for administering a pulmonary surfactant to any spontaneously breathing patient, more advantageously to a spontaneously breathing human neonate, preferably to pre-term neonate. In a particular embodiment, the device of the invention is used in combination with a catheter for administering a pulmonary surfactant to pre-term very-low-birth-weight neonates of 26-35 weeks gestational age (about 1-2 kg weight), that are spontaneously breathing, and demonstrate early signs of respiratory distress syndrome as indicated either by clinical signs and/or supplemental oxygen demand (fraction of inspired oxygen ((FiO2) >30%).

In an aspect, a laryngeal mask airway device comprises an exhalation channel having one of its ends in fluid communication with the distal end of the airway tube, and the other end being an outlet to air.

In an aspect, the laryngeal mask airway device is configured to enable the discharge of air from the outlet of the exhalation channel, in particular when positive pressure ventilation (PPV) and/or continuous positive airway pressure (CPAP) are applied. Positive pressure ventilation (PPV) can be applied e.g. by the ventilation equipment connected to the connector, such as mechanical ventilation equipment or self-inflating bags. The exhalation channel, in particular when PPV and/or CPAP are applied, promotes the formation of a particular flow of air within the device, whereby the exhaust air, such as the exhaled air of the patient, is flushed outside of the device, i.e. is flushed to the air, and is not trapped within the device, e.g. within the airway tube.

In an aspect, the outlet of the exhalation channel is close to the proximal end of the airway tube the proximal end of the airway tube.

In an aspect, the exhalation channel and the airway tube are in fluid communication through an exhalation orifice. The flow resistance of the exhalation channel can be controlled by selecting a suitable diameter of the exhalation orifice. Accordingly, in an aspect, the exhalation orifice is configured to control the flow resistance of the exhalation channel.

In an aspect, the exhalation orifice has a diameter comprised in the range of 0.4 to 4 mm, optionally of 0.8 to 2 mm. Such a diameter has been found to be particularly suitable to ensure that the positive pressure, for example applied by the ventilation equipment, is maintained, whilst a leakage flow rate sufficient to flush the dead volume of the laryngeal mask airway device over the course of a breathing cycle is enabled.

In an aspect, the airway tube delimits internally the exhalation channel, optionally by means of a dividing wall, or of a multi-lumen geometry of the airway tube, or by providing the exhalation channel as a smaller tube within the airway tube (smaller with respect to the of the airway tube).

In an aspect, the exhalation channel as herein disclosed in any of its aspects can be incorporated in the laryngeal mask airway device comprising the movable element, the control element, and the motion transmission device in any of its aspects as disclosed above.

Applicant verified that the laryngeal mask airway device comprising a exhalation channel according to the invention allows improvement of gas exchange in patients and their overall breathing. Indeed, with respect to conventional devices not comprising the exhalation channel, re-breathing of exhaled air (rich in $CO_2$) is reduced, as the exhaled air (which may be trapped within the airway lines of conventional devices) is flushed to the air by the exhalation channel.

Definitions

With the term "pulmonary surfactant" it is meant an exogenous pulmonary surfactant administered to the lungs that could belong to one of the following classes:

i) "modified natural" pulmonary surfactants which are lipid extracts of minced mammalian lung or lung lavage;

ii) "artificial" pulmonary surfactants which are simply mixtures of synthetic compounds, primarily phospholipids and other lipids that are formulated to mimic the lipid composition and behavior of natural pulmonary surfactant; they are devoid of pulmonary surfactant proteins;

iii) "reconstituted" pulmonary surfactants which are artificial pulmonary surfactants to which have been added pulmonary surfactant proteins/peptides isolated from animals or proteins/peptides manufactured through recombinant technology.

The term "non-invasive ventilation" (NIV) procedure defines a ventilation modality that supports breathing without the need for intubation.

Positive pressure ventilation (PPV) is the provision of air under pressure by a mechanical ventilation equipment, a machine designed to improve the exchange of air between the lungs and the atmosphere.

Continuous positive airway pressure (CPAP) is a form of non-invasive positive airway pressure ventilation, which applies mild air pressure on a continuous basis to keep the airways continuously open in people who are not able to breathe spontaneously on their own.

The term "prophylaxis" refers to the use for reducing the occurrence of the disease, while the term "treatment" refers to the use for palliative, curing, symptom-allievating, symptom-reducing, disease regression-inducing therapy.

The terms "newborn" and "neonate" are used as synonimous.

The term "pre-term neonate" refers to a neonate whose birth occurs earlier than 37 weeks gestational age.

The terms "proximal" (from Latin 'proximus', meaning 'nearest') and "distal" (from Latin 'distare', meaning 'to stand away from') are used to describe parts of a feature that are close to or distant from the main mass of the body, respectively.

As used herein, the terms "proximal" and "distal" refers to parts that are close to or distant from the user/clinician using the laryngeal mask airway device.

As used herein, the term "flexible" referred to the airway tube means that the airway tube deforms when inserted into the oropharynx of the patient due to the anatomy.

As used herein, the term "elastically flexible" referred to the catheter means that the catheter may be deflected by the movable element and return to its previous configuration when the force exerted by the movable element is removed.

DESCRIPTION OF THE DRAWINGS

FIG. 7 shows some elements of the portion of FIG. 4;

FIG. 8 shows another element of the laryngeal mask airway device in a first configuration;

FIG. 9 shows the element of FIG. 8 in a second configuration;

DETAILED DESCRIPTION

Figure 1:
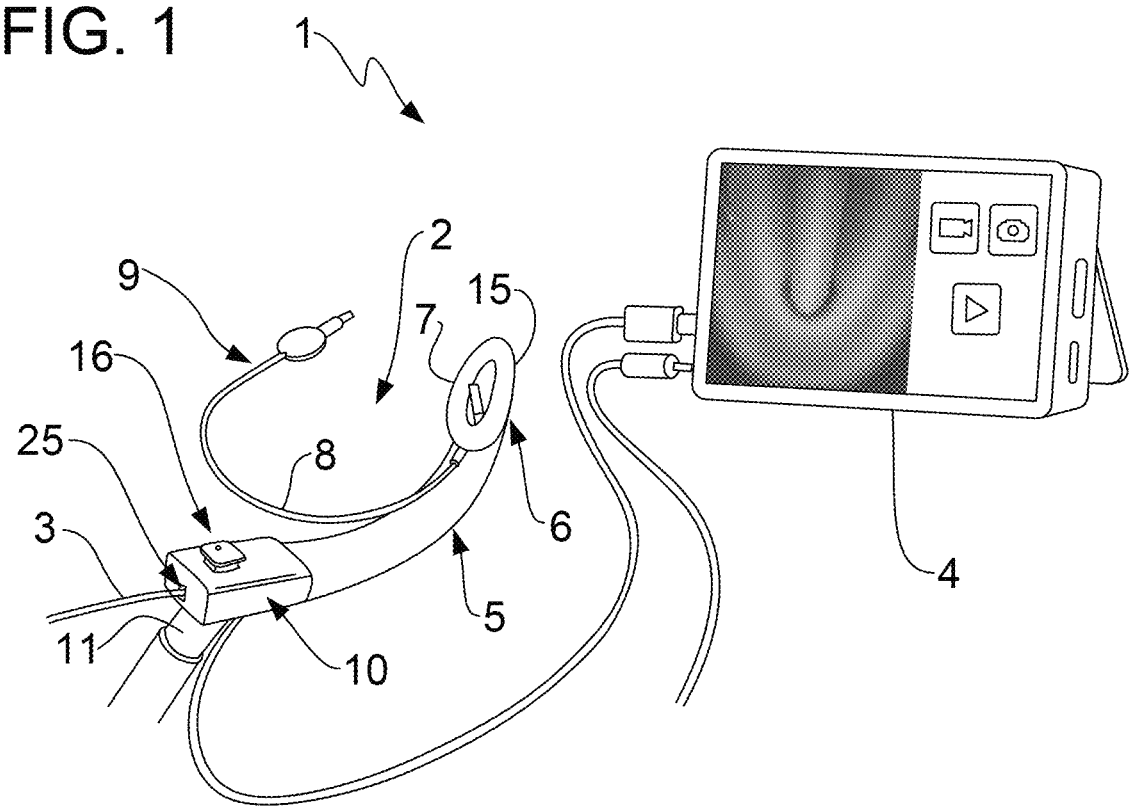
FIG. 1 shows a laryngeal mask airway device assembly according to the present invention.

With reference to the appended drawings, FIG. 1 shows a laryngeal mask airway device assembly 1 according to the present invention.

The assembly 1 comprises a laryngeal mask airway device 2, a catheter 3 and an electronic control unit provided with an electronic display screen 4.

The laryngeal mask airway device 2 and the catheter 3 may be part of a kit in a package.

A catheter 3 for minimally invasive endotracheal administration of a pulmonary surfactant may be used. The catheter 3 may be of polyurethane or silicone, has for example a diameter of 3.5, 4.0 or 5.0 French (Fr) and a length of 20 cm.

The laryngeal mask airway device 2 comprises an airway tube 5 having a proximal end and a distal end.

The airway tube 5 is curved, anatomically shaped and flexible, to reduce forces on the anatomy of the patient P. By way of example, the airway tube 5 may be made of PVC, silicone, elastomer or combination of multiple materials.

Figure 2:
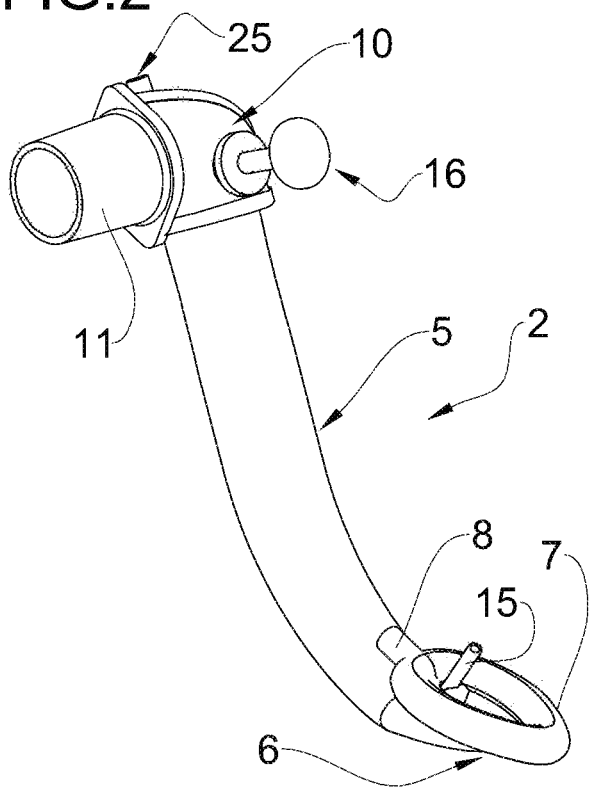
FIG. 2 shows a perspective view of an embodiment of a laryngeal mask airway device according to the present invention.
Figure 3:
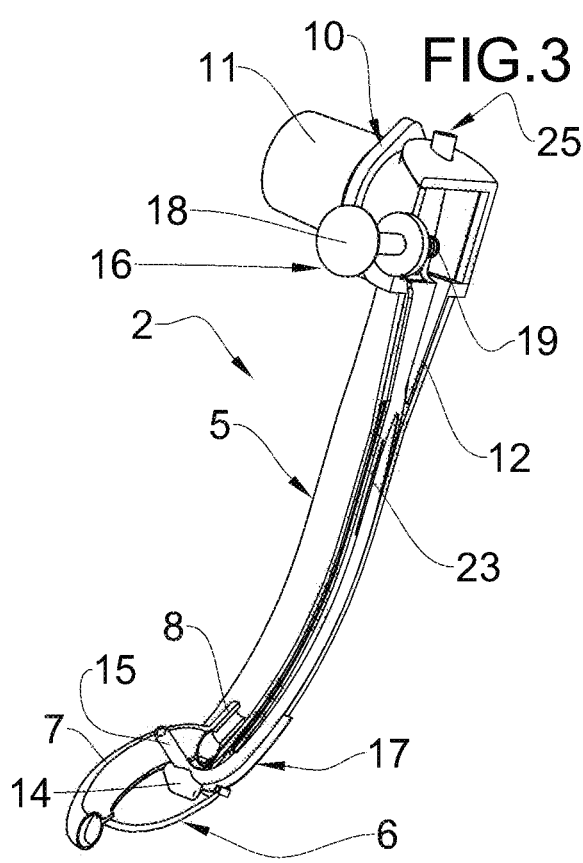
FIG. 3 shows a perspective and sectioned view of the laryngeal mask airway device of FIG. 2.
Figure 4:
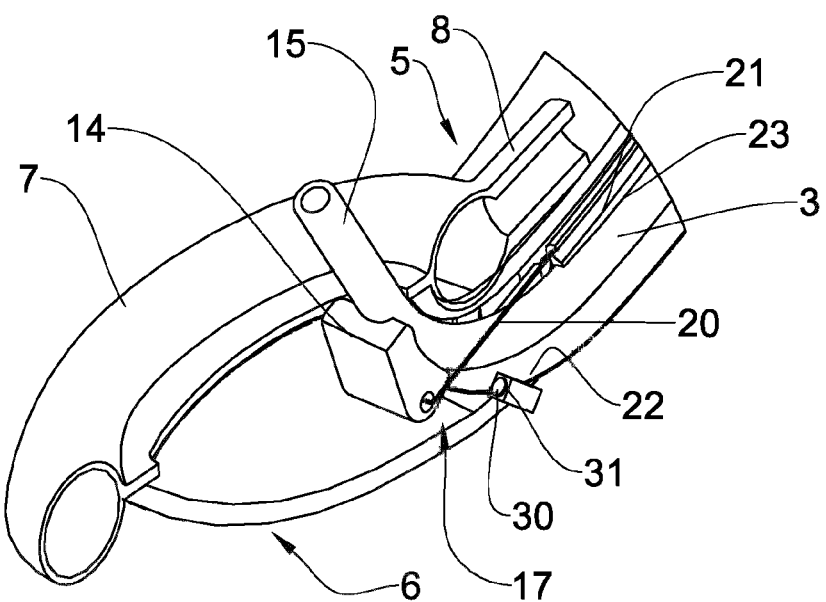
FIG. 4 is an enlarged and sectioned view of a portion of the laryngeal mask airway device of FIG. 2.

A laryngeal mask 6 is placed at the distal end of the airway tube 5 and it is shaped like a cup or bowl. An inflatable cuff 7 is disposed on an edge of the cup or bowl and it is shaped like a ring to form a seal around the glottis of a patient P. The inflatable cuff 7 is connected to an inflation tube 8 of an inflation line 9. Only part of the inflation tube 8 is shown in FIGS. 2, 3 and 4. In alternative embodiments, not shown, the inflation tube 8 may be joined to the airway tube 5 or may be fashioned in the airway tube 5. The inflation line 9 allows the cuff 7 to be inflated and deflated using for example a syringe, not shown.

Shapes and dimensions of the airway tube 5, the laryngeal mask 6 and the inflatable cuff 7 may be manufactured as a function of the patient (e.g. newborn, child or adult). Preferably, the laryngeal mask airway device 2 are manufactured in different sizes that are dimensioned to fit a range of neonatal patients, which may include full-term newborns to very premature newborns.

A box-like casing 10 defines the proximal end of the airway tube 5. The box-like casing 10 may be made of polypropylene, polycarbonate, ABS, polystyrene, HDPE, LDPE, nylon and it is preferably stiffer than the rest of the airway tube 5. The box-like casing 10 supports a connector 11 shaped like a tubular portion protruding from a side of the box-like casing 10.

The airway tube 5 delimits internally a ventilation conduit 12 which opens in the bowl of the laryngeal mask 6 and is in fluid communication with the connector 11. One end of the ventilation conduit 12 opens into the bowl and the other end in the box-like casing 10.

In the illustrated embodiment, the box-like casing 10 delimits internally a chamber 13 in fluid communication with the connector 11 and with the ventilation conduit 12.

The connector 11 is in fluid communication with the laryngeal mask 6 through the chamber 13 and through the ventilation channel 12 of the airway tube 5 and it is configured to be connected to a ventilation equipment, not shown, to provide e.g. positive pressure ventilation (PPV).

A movable element 14 is placed in the laryngeal mask 6 and it is configured to steer a tip 15 of the catheter 3 passing through the airway tube 5 when said catheter 3 protrudes in the laryngeal mask 6. A control element 16 and a motion transmission device 17 are incorporated within the airway tube 5 to control the position of the movable element 14. The motion transmission device 17 is operatively connected to the movable element 14 and to the control element 16 to move the movable element 14 and to steer the tip 15 of the catheter 3 by manually acting on the control element 16.

Figure 5:
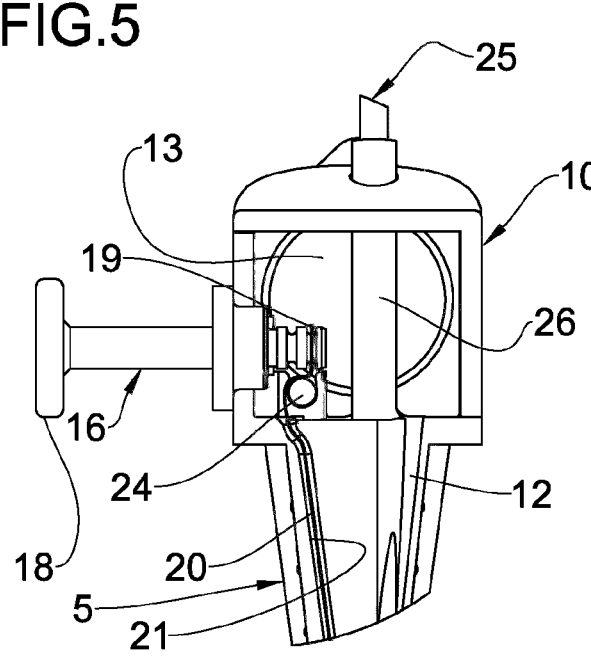
FIG. 5 is an enlarged and sectioned view of another portion of the laryngeal mask airway device of FIGS. 1 and 2 in a first configuration.

In the illustrated and not limiting embodiment, the control element 16 comprises a shaft slidably inserted through an aperture fashioned in the box-like casing 10. The shaft comprises (FIGS. 3, 5 and 6) an external portion 18 protruding from the box-like casing 10 and configured to be handled by a user/clinician and an internal portion 19 placed inside a housing delimited by the box-like casing 10 and connected to the motion transmission device 17. The control element 16 is therefore mounted on the proximal end of the airway tube 5. The housing and the chamber 13 may at least in part coincide.

Figure 6:
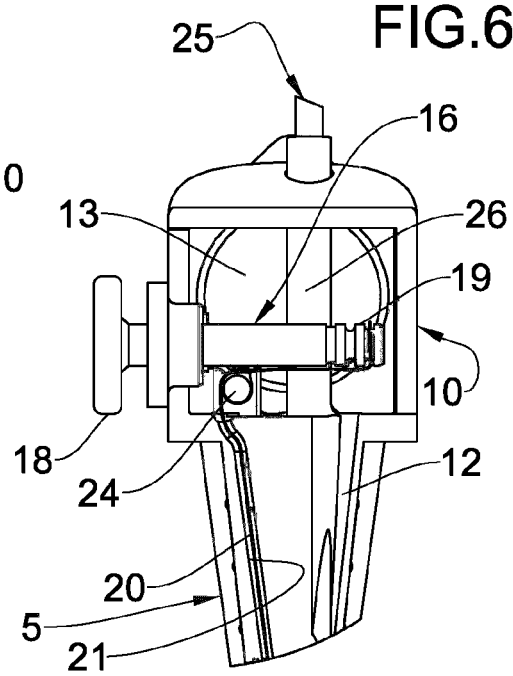
FIG. 6 is the portion of FIG. 5 in a second configuration.

The external portion 18 comprises a head, shaped like a button, which allows the user/clinician to pull or push the shaft and to axially move it between a first position and a second position. In the first position, the shaft is mainly extracted from the box-like casing 10 (FIG. 5) and in the second position the shaft is mainly retracted in the box-like casing 10 (FIG. 6).

The internal portion 19 comprises (FIGS. 5 and 6) a grip part with grooves to hook a proximal extremity of a cord or wire 20 belonging to the motion transmission device 17.

The motion transmission device 17 is a mechanical device comprising the mentioned cord 20 which is positioned in a passage 21 developing inside the airway tube 5 from the box-like casing 10 to the laryngeal mask 6. In other embodiments, not shown, in lieu of the single passage 21, the cord 20 is guided through a plurality passage sections.

The motion transmission device 17 further comprises a leaf spring 22 placed inside the ventilation duct 12 and close to the distal end of the airway tube 5. The leaf spring 22 comprises a part joined to the airway tube 5 whilst an end of the leaf spring 22 is cantilevered and protrudes out of the end of the ventilation duct 12 and into the bowl (FIGS. 4 and 7).

The leaf spring 22 is located on a side of the ventilation channel 12 of the airway tube 5 opposite the passage 21 for the cord 20 and the catheter 3 passes between the cord 20 and the leaf spring 22. In particular, the airway tube 5 delimits a guide channel 23 for the catheter 3 to guide the catheter 3 towards the bowl of the laryngeal mask 6. The leaf spring 22 may also be joined to the tubing delimiting the guide channel 23.

In other embodiments, not shown, a plurality of guide elements are disposed along the airway tube 5 in lieu of the guide channel 23, e.g. on an inner wall of the ventilation conduit 12.

As shown in FIGS. 3, 4, 5 and 6, the airway tube 5 is internally shaped to delimit the ventilation channel 12, the passage 21 for the cord 20 and the guide channel 23 for the catheter 3. The ventilation channel 12, the passage 21 and the guide channel 23 are distinct and parallel to each other. The guide channel 23 is placed between the leaf spring 22 and the passage 21.

The movable element 14 is a sort of pad placed in the bowl and mounted on the end of the leaf spring 22. A distal extremity of the cord 20 is linked to the movable element 14. In other embodiments, not shown, the leaf spring 22 and the movable element 14 are made in one piece as a single item.

A deflection element 24, shaped like a bar, is mounted inside the box-like casing 10 and the cord 20 coming from the passage 21 is partly wound around said deflection element 24 before hooking to the internal portion 19.

When the shaft is in the first position (FIG. 5), the movable element 14 is placed in a respective first position in which it lies against an inner surface of the bowl of the laryngeal mask 6. The leaf spring 22 is in a rest configuration and the cantilevered end of the leaf spring 22 too lies against the inner surface of the bowl of the laryngeal mask 6. If the tip 15 of the catheter 3 is present, it lies against the movable element 14.

When the user/clinician pushes the shaft to axially move it towards the second position, the cord 20 is pulled. The movable element 14 is pulled by the cord 20 and the leaf spring 22 is elastically deflected. Therefore, the movable element 14 is pulled by the control element 16 through the cord 20 in opposition to an elastic force exerted by the leaf spring 22. The second position of the shaft corresponds to a second position of the movable element 14, in which the movable element 14 protrudes into the bowl of the laryngeal mask 6 and the tip 15 of the catheter 3 is deflected by the movable element 14 (FIG. 4).

Adjusting manually the position of the shaft between the first and second position allows to steer and direct the tip 15 of the catheter 3.

The leaf spring 22 returns to its start position/configuration when the action on the control element 16 is released and the movable element 14 returns to the first position.

In other embodiments, not shown, the motion transmission device 17 may comprise other mechanical elements, like rods or similar, connecting the movable element 14 to the control element 16.

In other embodiments, not shown, the leaf spring 22 may be absent and the movable element 14 remains in the second position and/or must be moved, through the control element 16 and the motion transmission device 17, from the first position to the second position and from the second position to the first position.

The box-like casing 10 is provided with a catheter port 25 for inserting the catheter 3 through the guide channel 23. In the illustrated embodiment, the catheter port 25 is placed on a top face of the box-like casing 10 opposite the airway tube 5. In other embodiments, not shown, the catheter port 25 is placed on the side of the box-like casing 10 to face the user/clinician and the connector 11 is placed on the top face of the box-like casing 10 opposite the airway tube 5.

The catheter port 25 is connected to the guide channel 23 through a tubular section 26 passing through the housing and/or the chamber 13 delimited by the box-like casing 10.

Figure 10:
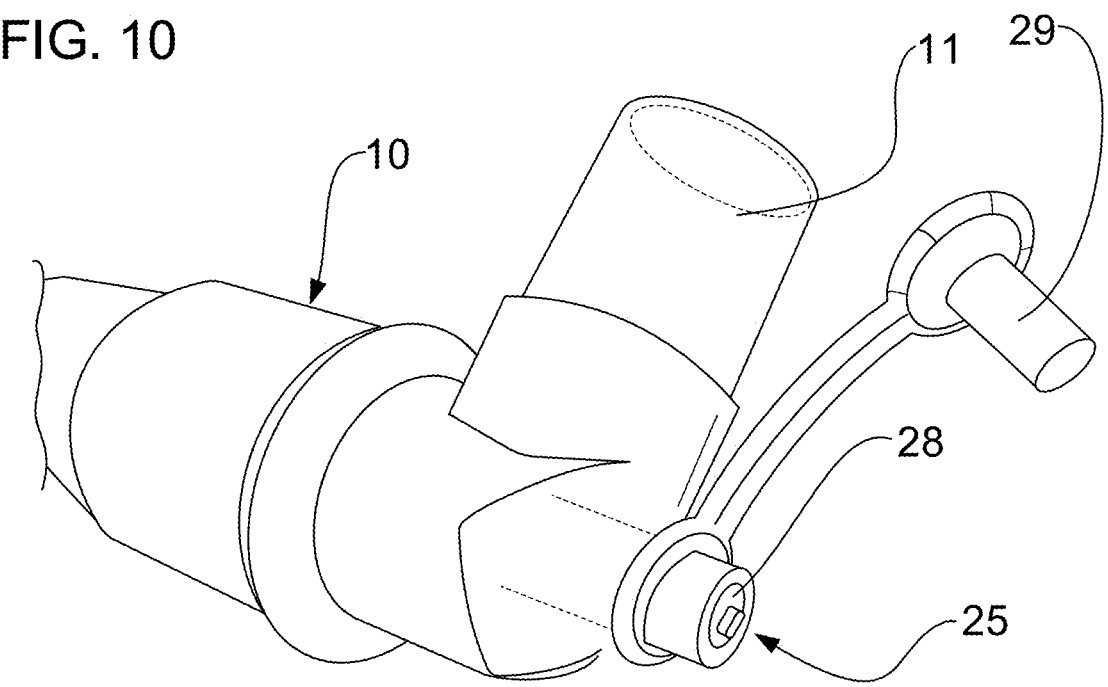
FIG. 10 shows another enlarged portion of the laryngeal mask airway device of FIG. 2 according to an alternative embodiment.
Figures 11, 12:
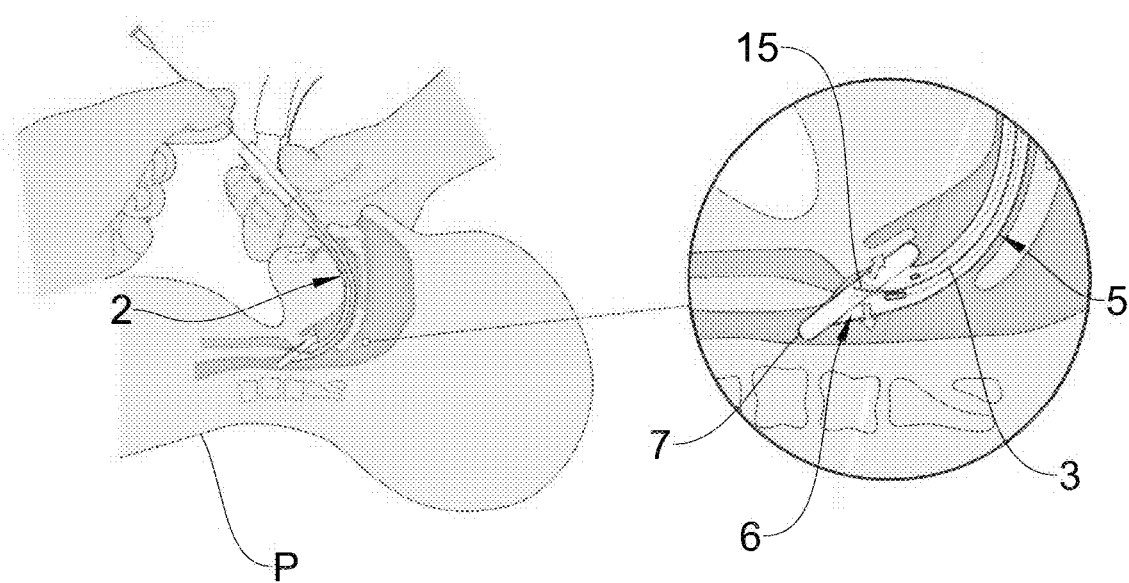
FIG. 11 shows a step of a method for administering a medicament through a laryngeal mask airway device according to the invention.
FIG. 12 shows an enlarged part of FIG. 11.

In the embodiment of FIGS. 5, 6, 8 and 9, the catheter port 25 comprises a self-sealing opening 27 which allows to insert the catheter 3 (FIG. 8) whilst preventing air leakage. The self-sealing opening 27 may be a 'normally closed' elastomeric valve, for example a silicone 'duckbill' valve. In the alternative embodiment of FIG. 10, the catheter port 25 comprises an 'o-ring' 28 and a sealing cap 29.

The laryngeal mask airway device 2 further comprises a camera 30 and an illumination source 31 which are placed at the distal end and inside the bowl of the laryngeal mask 6. The camera 30 and the illumination source 31 are positioned to give a view of the vocal cords and of the catheter tip 15 as it advances into the laryngeal inlet. The camera 30 and the illumination source 31 of the illustrated embodiment are placed at the end of the ventilation conduit 12 opening into the bowl and face outwards the ventilation channel 12 to frame the movable element 14 and the catheter tip 15.

The camera 30 may be a CMOS sensor-based camera module. The illumination source may be an LED.

The camera 30 and the illumination source 31 may be part of an integrated visualization system which is connected to the electronic display screen 4 of the electronic control unit through a wiring in part integrated in the airway tube 5.

The power and data signals for the camera 30 and illumination source 31 are transmitted via conductors which emerge at the proximal end of the airway tube 5. These conductors (which may arranged in a cable assembly) are then connected to the electronic control unit. The electronic control unit converts the signal from the camera module into an image which is displayed on the electronic display screen 4.

In a different embodiment, not shown, the camera 30 and the illumination source 31 may be part of an endoscope, e.g. a fibre-optic endoscope, passing through another dedicated channel fashioned in the airway tube 5. The end of said dedicated channel face outwards the ventilation channel 12 and may be closed by a transparent cap to protect the endoscope whilst allowing the transmission of light. The endoscope may be removed from the dedicated channel and re-used.

In a different embodiment, not shown, a stand-alone light fiber or light guide for the illumination may be used.

The electronic display screen 4 presents a live view from the camera 30 to the user/clinician.

The laryngeal mask airway device assembly 1 may be, in part or in-toto, reusable or disposable.

According to one embodiment, the airway tube 5 with the cuff 7 are disposable and are removably connected to the box-like casing 10. The passage 21 for the cord 20, the guide channel 23 for the catheter 3, the movable element 14, the spring 22 and the cord 20 are linked to the box-like casing 10 and may be extracted from the airway tube 5 when said airway tube 5 is disconnected from the box-like casing 10. In the illustrated embodiment (see FIGS. 3 to 6), the passage 21 for the cord 20 and the guide channel 23 for the catheter 3 are delimited by tubings joined to the box-like casing 10. The spring 22 is joined to the tubing of the passage 21 for the cord 20. The airway tube 5 is fitted on a proximal end of these tubings and may be removed.

The laryngeal mask airway device assembly 1 described above allows to administer a medicament according to a method of the present invention. In particular, the laryngeal mask airway device assembly 1 may be adopted to administer a surfactant to premature newborns suffering of Respiratory Distress Syndrome (RDS). However, the therapeutic method could also be intended for the prevention and/or treatment of any disease related to a surfactant-deficiency or dysfunction as well as of conditions in which respiratory distress may be present that include, but are not limited to, meconium aspiration and pulmonary infection.

Figure 13:
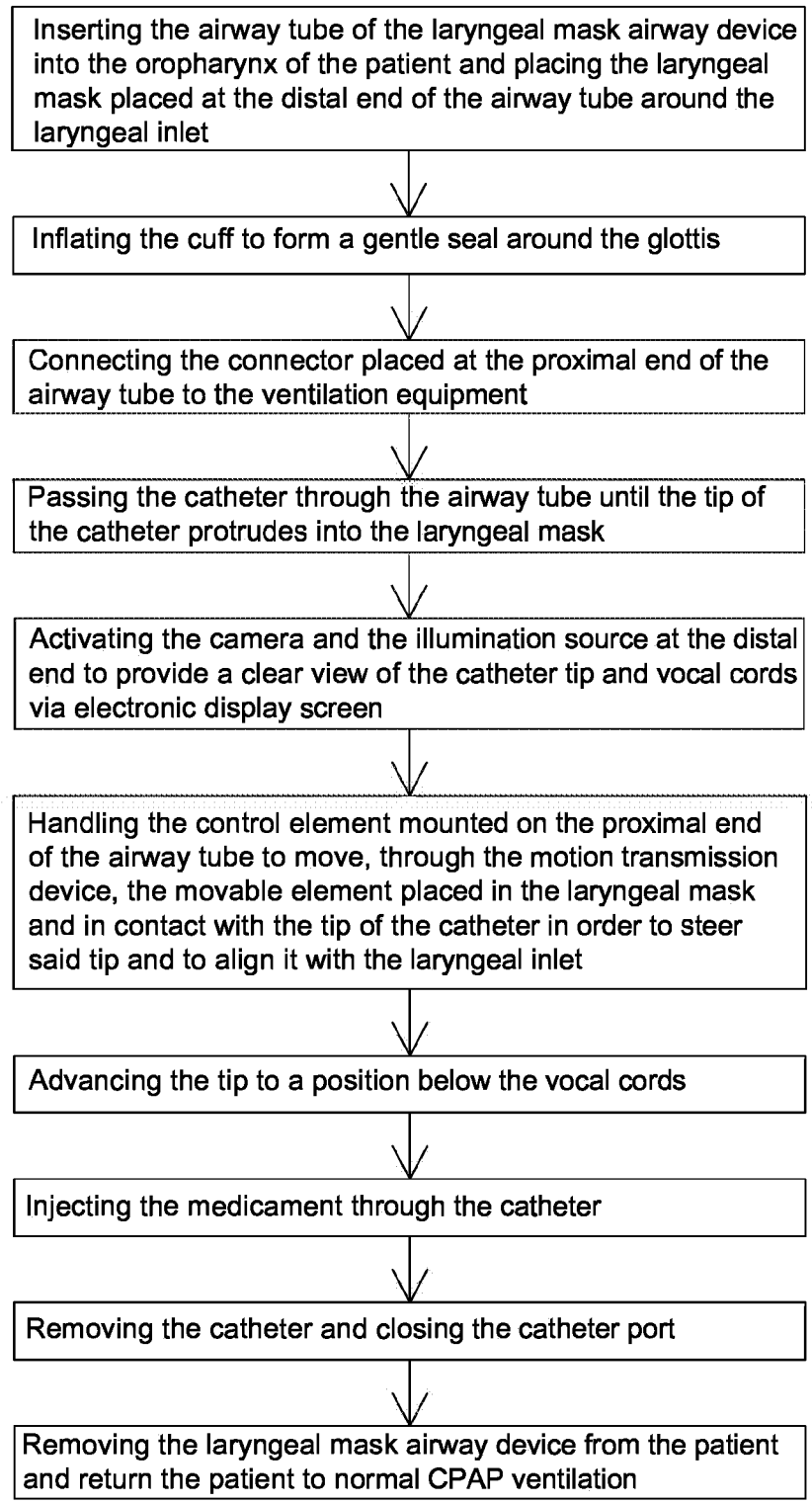
FIG. 13 is a flowchart of a method for administering a medicament through a laryngeal mask airway device according to the invention.

In accordance to the method of the invention (see flow-chart of FIG. 13), the airway tube 5 of the laryngeal mask airway device 2 is inserted into the oropharynx of the patient P and the laryngeal mask 6 is placed around the laryngeal inlet. The cuff 7 is then inflated to form a gentle seal around the glottis.

The connector 11 is connected to the ventilation equipment so that CPAP ventilation can be provided throughout the surfactant administration procedure.

The clinician passes the catheter 3 through the airway tube 5 until the tip 15 of the catheter 3 protrudes into the laryngeal mask 6 and abuts against the movable element 14.

The camera 30 and illumination source 31 at the distal end are activated to provide the clinician with a clear view of the catheter tip 15 and vocal cords, via the electronic display screen 4.

By grabbing the proximal end of the airway tube 5 and handling the control element 16 mounted on the proximal end of the airway tube 5, the clinician moves, through the motion transmission device 17, the movable element 14 and steers the tip 15 to align it with the laryngeal inlet without the need to manipulate the patient's anatomy or manoeuvre the laryngeal mask airway device in-situ.

The clinician advances the catheter tip 15 to a position below the vocal cords, using the live image to control and verify correct insertion.

Once the tip 15 is in the correct position, the clinician injects the surfactant through the catheter 3.

Following surfactant administration, the catheter 3 is removed and the catheter port 25 is closed. The laryngeal mask airway device 2 may be used to provide non invasive ventilation to recover bradycardia or hypoxia.

Finally, the laryngeal mask airway device 2 is removed from the patient P and the patient P can be returned to normal non invasive ventilation, e.g. via CPAP through nasal prongs.

Nasal CPAP may be applied at a pressure comprised between 2 and 8 cm $H_2O$, although the pressure can vary depending on the neonate age and the pulmonary condition. Other non-invasive ventilation procedures, such as nasal intermittent positive-pressure ventilation (NIPPV) and bi-level positive airway pressure (BiPAP) or high flow nasal cannula (HFNC), may alternatively be applied to the patients.

The physician shall choose the type of medicament, the type of non-invasive ventilation support, and the type of interface according to his experience and to the condition of the neonate such as the gestational age and severity of the disease.

Figure 14:
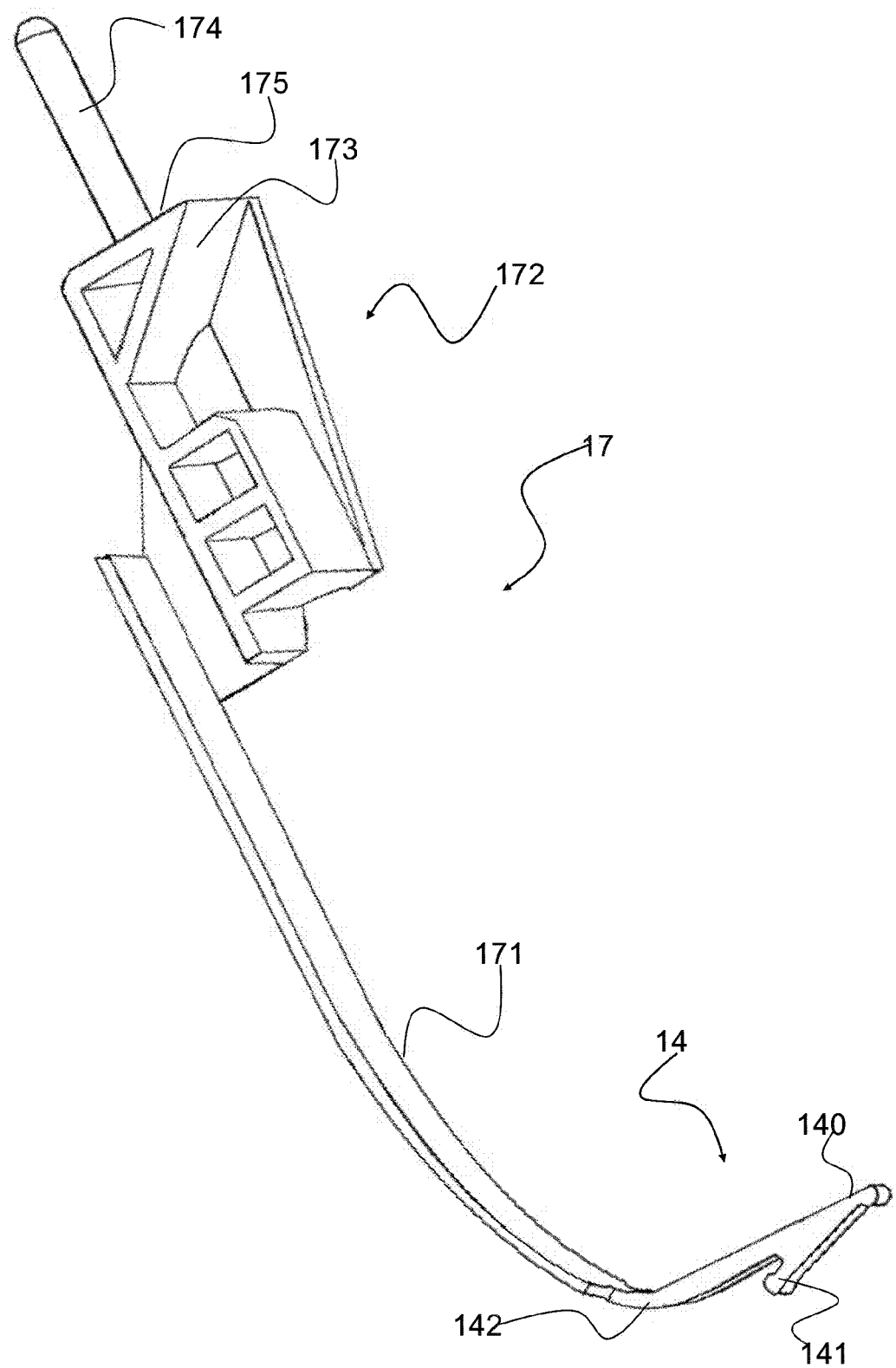
FIG. 14 shows a perspective view of the movable element and of the motion transmission device according to embodiments of the device.

FIG. 14 shows the motion transmission device 17 and the movable element 14 according to embodiments of the invention. In such embodiments, the motion transmission device 17 and the moveable element 14 are jointly attached as to form a single item, whereby movement of the motion transmission device 17 provides movement (rotation) of the moveable element 14. The motion transmission device 17 and the moveable element 14 are advantageously made of a flexible material, such as plastic, so that force/tension can be transmitted through at least part of the motion transmission device 17 and/or of the moveable element 14. The motion transmission device 17 comprises the stem 171 and the linking interface 172. The movable element 14 comprises the hooked tip 140, the anchor point 141 and the flexible section 142. The linking interface 172 has a wedge 173 that is arranged to engage with a respective wedge of the control element (not shown in FIG. 14). By acting the control element, e.g. pressing the control element, the respective wedge slides over the wedge 173, whereby the linking interface 172 (and the stem 171 as well) slide back, transmitting a tension force to the moveable element 14 that comprises the hooked tip 140. The hooked tip 140 is arranged in the device 1 to rotate about an axis when the motion transmission device 17 moves and thus when tension is transmitted to it. The rotation of the hooked tip 140 steers the tip of the catheter. Rotation of the hooked tip 140 is favored inter alia by the hinge formed between the anchor point 141 and a respective anchor point e.g. in the airway tube (not shown). Rotation of the hooked tip 140 is further favored by the flexible section 142, which is thinner at least with respect to the stem 171. The flexible section 142 is arranged within the device 1 to bend when tension is transmitted to the moveable element 14; movement of the motion transmission device 17 bends the flexible section 142, and rotation of the hooked tip 140 about the hinge formed by the anchor point 141 is obtained. According to the present embodiment, the motion transmission device 17 can further comprise a spring (not shown) which is mounted about a shaft 174 of the linking interface 172. The spring abuts at one of its ends against a surface of the interior wall of the box-like casing, and at the other end against a pushing surface 175. The spring is tensioned when the linking interface 172 slides back by acting the control element. The spring is discharged when the control element is released. Discharge of the spring causes the return of the motion transmission device 17, of the movable element 14 and of the control element to their start position/configuration. Accordingly, the hooked tip 140 is moveably arranged in the laryngeal mask airway device such that it can rotate (i.e. move) between a first position and a second position, in which it steers the tip of the catheter, wherein the control element is movable at least between a first position and a second position corresponding to the first position and the second position of the hooked tip. According to this embodiment, the motion transmission device 17 and the movable element 14, provided as a single item, are mechanically robust and simple to manufacture. Moreover, such a single item is suitable to be used in a flexible device such as the device 1, as the mechanism of the motion transmission device 17 and of the moveable element 14 do not rely on rigid members for transmission of force. Furthermore, the motion transmission device 17 according to this aspect has a particularly thin and compact profile; the laryngeal mask airway device 1 comprising such a motion transmission device 17 can thus be smaller than conventional laryngeal mask airway devices, so that it is particularly advantageous for its use with pre-term neonates. Finally, the spring-discharge enables actuation by a "press/release" input of the control element, which lends itself to one-handed operation with a single finger, freeing a user's other hand and greatly improving the ease of use of the device.

Figure 15:
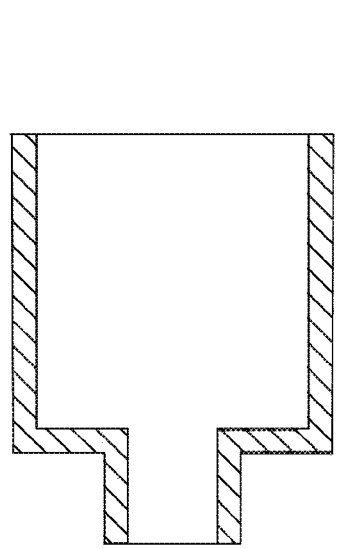
FIG. 15A shows a schematic section of a conventional connector according to prior art)
FIG. 15B shows a schematic section of a connector according to embodiments of the device.
Figure 15:
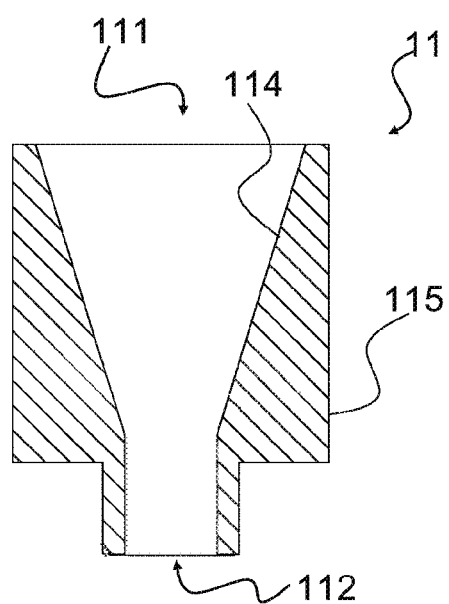

FIG. 15A shows schematic sections of a conventional connector according to prior art and FIG. 15B shows of a connector according to embodiments of the device 1 of the invention. In particular, FIG. 15A shows that internal walls of the conventional connectors narrow down abruptly from the bigger end, i.e. the end that engages with the ventilation equipment, to smaller end, i.e. the end that is connected to the airway tube. Such abrupt narrowing provides contraction to the flow of air and thus higher flow resistance with respect to the connector shown in FIG. 15B. Moreover, the dead volume of prior art connectors (e.g. the ones of FIG. 15A) is higher with respect to the dead volume of the connector according to embodiments of the device 1 (e.g. the one of FIG. 15B).

The connector 11 of FIG. 15B comprises external walls 115 and internal walls 114, the latter converging seamlessly from the first end 111 to the second end 112. The external wall 115 is configured to engage with respective standard female connectors of ventilation equipment. The geometry of the interior wall 114 provides a reduced flow resistance with respect to conventional connectors, such as the one of FIG. 15A. The geometry of the connector 11 also allows reducing the dead volume/space of the laryngeal mask airway device 1.

Figure 16:
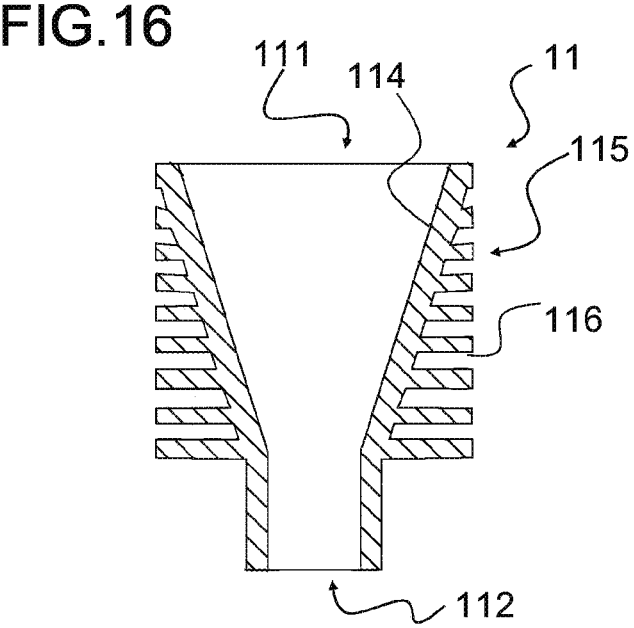
FIG. 16 shows a schematic section of another connector according to embodiments of the device.

FIG. 16 shows a schematic section of another connector 11 as herein described. The connector 11 of FIG. 16 comprises fins 116 that protrudes outwards from the interior wall 114. Such fins are flush with one another, and thus form the external wall 116 which is configured to engage with respective female standard connectors of ventilation equipment (for example as showed in FIG. 17). Moreover, the thickness of each fin is advantageously similar to the thickness of the internal walls, whereby the connector 1 can be easily manufactured e.g. by injection molding.

Figure 17:
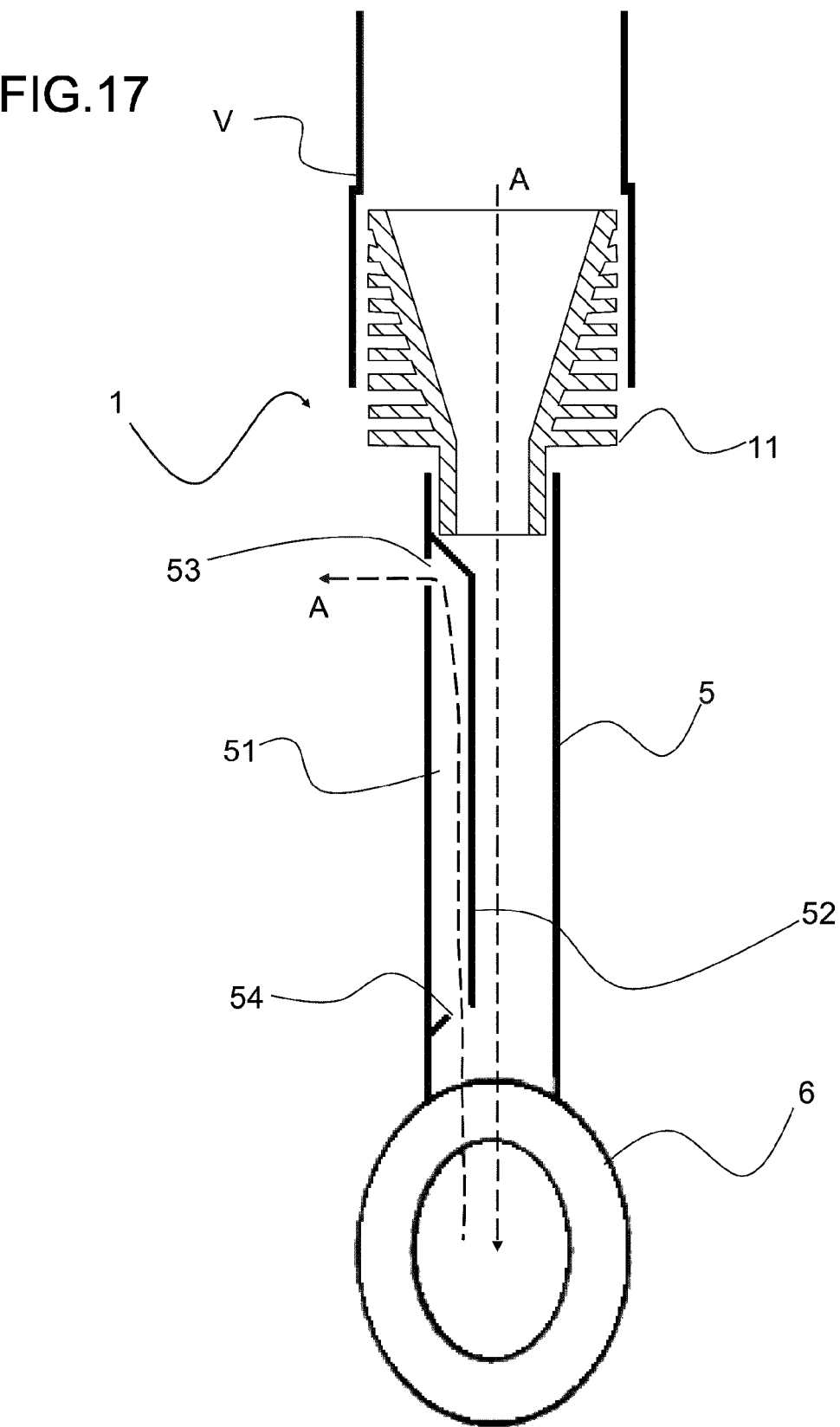
FIG. 17 shows a schematic view of embodiments of the laryngeal mask airway device that is engaged with a standard female connection of a ventilation equipment.

FIG. 17 shows a schematic view of an embodiment of the laryngeal mask airway device 1 comprising a connector 11 (represented as the connector of FIG. 16), an airway tube 5, a laryngeal mask 6, and exhalation channel 51. The device 1 is engaged with a standard female connection of a ventilation equipment V. The exhalation channel 51 is delimited within the airway tube 5 by means of a dividing wall 52. The exhalation channel 51 is in fluid connection with the distal end of the airway tube 5 through the exhalation orifice 54. The outlet 53 of the exhalation channel 51 allows exhalation the air within the device 1, e.g. the exhaled air of the patients, thereby re-breathing of exhaled air is substantially avoided. The present embodiment can advantageously provide a one-way flow of air that is similar to the one schematically represented by the dashed arrow A in FIG. 17, in particular when PPV is applied, e.g. by means of the ventilation equipment V. Such a flow of air favours the exhalation of exhaled air by the patient out of the outlet 53.

FIG. 17 also schematically shows the engagement between the external wall of the connector 11 (represented as the connector of FIG. 16) with the female standard connector of conventional ventilation equipment V.

The invention claimed is:

1. A laryngeal mask airway device, comprising:
an airway tube having a proximal end and a distal end;
a laryngeal mask placed at the distal end of the airway tube, wherein the distal end of the airway tube opens inside the laryngeal mask, wherein the laryngeal mask is configured to seal around a laryngeal inlet of a patient;
a connector placed at the proximal end or close to the proximal end of the airway tube, wherein the connector is in fluid communication with the laryngeal mask through the airway tube and is configured to be connected to a ventilation equipment;
a movable element placed in the laryngeal mask and configured to steer a tip of a catheter passing through the airway tube when said catheter protrudes in the laryngeal mask;
a control element;
a motion transmission device operatively connected to the movable element and to the control element to move the movable element and to steer the tip of the catheter by acting on the control element;
a casing defining the proximal end and supporting the connector and the control element,
wherein the casing comprises an aperture,
wherein the control element comprises a shaft slidably inserted through the aperture,
wherein the shaft is perpendicular to a longitudinal axis of the casing, and
wherein the shaft hooks to a cord of the motion transmission device by the slidable insertion; and
wherein the control element is mounted on the proximal end of the airway tube.

2. The laryngeal mask airway device according to claim 1, wherein the control element comprises at least one of a handle, a lever, a button and a joystick.

3. The laryngeal mask airway device according to claim 1, wherein the control element comprises an external portion protruding from the proximal end and configured to be handled by a user and an internal portion placed inside the proximal end and connected to the motion transmission device.

4. The laryngeal mask airway device according to claim 3, wherein the movable element is movable between a first position, in which it lies against an inner surface of the laryngeal mask, and a second position, in which it protrudes into the laryngeal mask to steer the tip of the catheter; wherein the control element is movable at least between a first position and a second position corresponding to the first position and the second position of the movable element.

5. The laryngeal mask airway device according to claim 3, wherein the cord is pulled when the control element moves towards the second position.

6. The laryngeal mask airway device according to claim 1, wherein the motion transmission device is a mechanical device inserted or incorporated within the airway tube.

7. The laryngeal mask airway device according to claim 1, wherein the motion transmission device comprises a cord and a leaf spring.

8. The laryngeal mask airway device according to claim 7, wherein the airway tube comprises or delimits a passage for the cord.

9. The laryngeal mask airway device according to claim 7, wherein the leaf spring is located on a side of the airway tube opposite the cord; wherein the catheter passes between the cord and the leaf spring.

10. The laryngeal mask airway device according to claim 1, comprising a guide element for the catheter extending along the airway tube from the proximal end and the distal end; wherein the guide element is a guide channel.

11. The laryngeal mask airway device according to claim 1, wherein the proximal end has a catheter port for inserting the catheter wherein the catheter port comprises a self-sealing opening or a cap to close said catheter port.

12. The laryngeal mask airway device according to claim 1, comprising a camera and an illumination source placed at the distal end and inside the laryngeal mask.

13. The laryngeal mask airway device according to claim 12, comprising an electronic display screen connected to the camera.

14. The laryngeal mask airway device according to claim 1, wherein said laryngeal mask airway device further comprises an exhalation channel having one of its ends in fluid communication with the distal end of the airway tube, and its other end being an outlet to air.

15. The laryngeal mask airway device according to claim 14, the outlet of the exhalation channel is close to the proximal end of the airway tube.

16. The laryngeal mask airway device according to claim 14, wherein said exhalation channel and said airway tube are in fluid communication through an exhalation orifice having a diameter comprised in the range of 0.4 to 4 mm.

17. The laryngeal mask airway device according to claim 14, wherein said airway tube delimits internally said exhalation channel.

18. The laryngeal mask airway device according to claim 1, wherein said connector:
is configured to be connected at a first end to said ventilation equipment and at a second end to said airway tube,
said second end having a smaller section area than a section area of the first end, and
said first end being in fluid communication with said second end, said connector further comprising external walls configured to engage with said ventilation equipment, and
internal walls delimiting the internal space of the connector, said internal walls converging seamlessly from said first end to said second end.

19. The laryngeal mask airway device according to claim 18, wherein said external walls comprise one or more fins, said one or more fins protruding outwards from said internal walls.

20. The laryngeal mask airway device according to claim 19, wherein said one or more fins comprises at least two fins and protrude from the internal walls for a length such that they are flush with one another.

21. The laryngeal mask airway device according to claim 1, wherein the casing comprises a catheter port.

22. A laryngeal mask airway device, comprising:
an airway tube having a proximal end and a distal end;
a laryngeal mask placed at the distal end of the airway tube, wherein the distal end of the airway tube opens inside the laryngeal mask, wherein the laryngeal mask is configured to seal around a laryngeal inlet of a patient;

a connector placed at the proximal end or close to the proximal end of the airway tube, wherein the connector is in fluid communication with the laryngeal mask through the airway tube and is configured to be connected to a ventilation equipment; a movable element placed in the laryngeal mask and configured to steer a tip of a catheter passing through the airway tube when said catheter protrudes in the laryngeal mask;

a control element;

a motion transmission device operatively connected to the movable element and to the control element to move the movable element and to steer the tip of the catheter by acting on the control element;

wherein the control element is mounted on the proximal end of the airway tube, wherein the motion transmission device comprises a cord and a leaf spring, and wherein the movable element is mounted to an end of the leaf spring and an extremity of the cord is linked to the movable element or to said end of the leaf spring so that the leaf spring is elastically deflected by pulling the cord.

23. A laryngeal mask airway device, comprising:

an airway tube having a proximal end and a distal end;

a laryngeal mask placed at the distal end of the airway tube, wherein the distal end of the airway tube opens inside the laryngeal mask, wherein the laryngeal mask is configured to seal around a laryngeal inlet of a patient;

a connector placed at the proximal end or close to the proximal end of the airway tube, wherein the connector is in fluid communication with the laryngeal mask through the airway tube and is configured to be connected to a ventilation equipment;

a movable element placed in the laryngeal mask and configured to steer a tip of a catheter passing through the airway tube when said catheter protrudes in the laryngeal mask;

a control element;

a motion transmission device operatively connected to the movable element and to the control element to move the movable element and to steer the tip of the catheter by acting on the control element, wherein said motion transmission device comprises a stem and said movable element comprises a hooked tip, said stem being jointly attached at its distal end to said hooked tip, whereby said stem and said hooked tip are made in one piece as a single item, wherein said stem is moveably arranged in the laryngeal mask airway device such that it moves at least along an axis parallel to the longitudinal axis of the airway tube when the control element is operated, wherein said hooked tip is moveably arranged in the laryngeal mask airway device such that it rotates about an axis when the stem moves, and wherein the motion transmission device comprises a linking interface jointly attached to a proximal end of said stem, whereby said stem, said hooked tip and said linking interface are made in one piece as single item, said linking interface being linked to said control element, whereby actuating said control element causes movement of said linking interface, of said stem, and rotation of said hooked tip; and a casing defining the proximal end and supporting the connector and the control element;

wherein the control element is mounted on the proximal end of the airway tube.

24. The laryngeal mask airway device according to claim 23, wherein said linking interface has a wedge contacting a respective wedge of said control element, said wedges being arranged to be slidingly moveable relative to each other, whereby movement of the control element from a first position to a second position causes movement of the linking interface.

25. The laryngeal mask airway device according to claim 23, wherein said hooked tip comprises an anchor point configured to contact a respective anchor point positioned at the distal end of the airway tube, whereby the anchor point of the hooked tip and the respective anchor point form a hinge about which the hooked tip rotates.

26. A laryngeal mask airway device, comprising:

an airway tube having a proximal end and a distal end;

a laryngeal mask placed at the distal end of the airway tube, wherein the distal end of the airway tube opens inside the laryngeal mask, wherein the laryngeal mask is configured to seal around a laryngeal inlet of a patient;

a connector placed at the proximal end or close to the proximal end of the airway tube, wherein the connector is in fluid communication with the laryngeal mask through the airway tube and is configured to be connected to a ventilation equipment; a movable element placed in the laryngeal mask and configured to steer a tip of a catheter passing through the airway tube when said catheter protrudes in the laryngeal mask;

a control element;

a motion transmission device operatively connected to the movable element and to the control element to move the movable element and to steer the tip of the catheter by acting on the control element;

wherein the control element is mounted on the proximal end of the airway tube, wherein said motion transmission device comprises a stem and said movable element comprises a hooked tip, said stem being jointly attached at its distal end to said hooked tip, whereby said stem and said hooked tip are made in one piece as a single item, and wherein said hooked tip comprises a flexible section jointly attached to the distal end of the stem, said flexible section being thinner with respect to the stem.

* * * * *